United States Patent [19]

Uda et al.

[11] Patent Number: 4,773,935
[45] Date of Patent: Sep. 27, 1988

[54] MOISTURE SENSOR CONTAINING CELLULOSE ACETATE BUTYRATE

[75] Inventors: Kazutaka Uda; Masaya Hijikigawa, both of Nara, Japan

[73] Assignee: Sharp Kabushiki Kaisha, Osaka, Japan

[21] Appl. No.: 885,311

[22] Filed: Jul. 14, 1986

Related U.S. Application Data

[63] Continuation of Ser. No. 707,588, Mar. 4, 1985, abandoned.

[30] Foreign Application Priority Data

Mar. 8, 1984 [JP] Japan ................. 59-46321

[51] Int. Cl.⁴ .......................... C08L 1/12; H01L 7/00
[52] U.S. Cl. ................... 106/181; 106/196; 106/169; 73/29; 204/430; 338/35; 536/65
[58] Field of Search ........ 106/181, 196, 169; 204/430; 536/80, 64, 65; 73/29; 338/35

[56] References Cited

U.S. PATENT DOCUMENTS

| | | | |
|---|---|---|---|
| 2,380,896 | 7/1945 | Kaszuba | 536/64 |
| 3,475,356 | 10/1969 | Davis et al. | 260/13 |
| 3,631,023 | 12/1971 | Horne | 260/229 |
| 3,671,913 | 6/1972 | Mamiya | 338/35 |
| 3,673,084 | 6/1972 | King | 210/23 |
| 3,983,527 | 9/1976 | Ohsato et al. | 338/35 |
| 4,404,347 | 9/1983 | Nakamura | 527/300 |
| 4,482,581 | 11/1984 | Lorin et al. | 427/79 |
| 4,520,341 | 5/1985 | Miyoshi et al. | 338/35 |
| 4,562,725 | 1/1986 | Oka et al. | 73/29 |

OTHER PUBLICATIONS

Chem Abst: 52:14,156i Beever.
Journal of Paint Tech. "Influence of Polyisocyanates on Physically Drying Systems" Mennicken, vol. 43, No. 552, pp. 83–88 (1971).
Chemical Abstracts, vol. 85, abstract 125977k (1976).
M. Hijikigawa, Proceedings of the Second International Meeting on *Chemical Sensors*, Table of Contents, pp. 101–108 (1986).
An MOS Device for AC Measurement of Surface Impedance with Application to Moisture Monitoring; Steven L. Garverick and Stephen D. Senturia, IEEE Transactions on Electron Devices, vol. ED-29, No. 1, Jan. 1982.

*Primary Examiner*—Theodore Morris
*Attorney, Agent, or Firm*—Spencer & Frank

[57] ABSTRACT

A moisture sensitive material prepared by cross-linking cellulose acetate butyrate with at least one compound selected from the group consisting of compounds containing two or more isocyanate groups; copmpounds containing two or more epoxy groups; compounds containing two or more carboxyl groups; and acid anhydrides of carboxylic acids.

19 Claims, 2 Drawing Sheets

MOISTURE SENSOR CONTAINING CELLULOSE ACETATE BUTYRATE

This is a continuation of application Ser. No. 707,588 filed Mar. 4, 1985 now abandoned.

BACKGROUND OF THE INVENTION

1. Field of the Invention

The present invention relates to a moisture sensitive material comprising a crosslinked polymer film, which detects variation of humidity in the atmosphere with a variation in the dielectric constant of the crosslinked polymer film.

2. Description of the Prior Art

As a moisture sensitive material wherein an electrical resistance or an electrical capacity varies depending upon a variation of humidity or water vapor in the atmosphere, there have been, for example, a moisture sensitive material having a sintered body of metal oxides such as iron oxide ($Fe_2O_3$ or $Fe_3O_4$), tin oxide ($SnO_2$), etc., or a metal oxide film; a moisture sensitive material having a hydrophilic polymer film or a polyelectrolyte; a moisture sensitive material having an electrolyte salt such as lithium chloride (LiCl); and a moisture sensitive material having a hygroscopic resin or polymer film in which conductive particles or fibers such as carbon are dispersed.

While a moisture sensor containing a metal oxide film or a hydrophilic polymer film has generally a wide moisture-sensitivity range, its resistance varies exponentially, responding to relative humidity in the atmosphere. A moisture sensor containing a metal oxide has an excellent heat resistance and responds rapidly, but it has a high temperature resistance coefficient. Especially, moisture sensors having a sintered body of metal oxides are inferior in reproducibility and/or interchangeability of the moisture sensitive characteristic thereof because the moisture sensitive characteristic depends upon the constituents of the sensor to a great extent. A moisture sensor having an electrolyte salt such as lithium chloride detects only humidity in a narrow range and if it is allowed to stand in a high humidity atmosphere for a long period of time, the electrolyte salt therein is eluted or diluted resulting in deterioration of the moisture sensitive characteristic of the sensor, and accordingly it cannot be used for determination of high humidity. A moisture sensor having a hygroscopic resin or the like, in which conductive particles or fibers are dispersed, cannot detect a humidity in a wide range because it exhibits a steep variation of the resistance thereof in a high humidity atmosphere, while it is not sensitive to low humidity. Also a moisture sensor having a hydrophilic polymer film or a polyelectrolyte film is inferior in humidity resistance, water resistance and durability, while it is advantageous in that it operates in a wide moisture sensitive range, has a rapid moisture sensitive response, a simple structure, and is easily produced at low cost.

SUMMARY OF THE INVENTION

The moisture sensitive material of this invention which overcomes the above-discussed disadvantages of the prior art, is prepared by cross-linking cellulose acetate butyrate with at least one compound selected from the group consisting of compounds containing two or more isocyanate groups; compounds containing two or more epoxy groups; compounds containing two or more carboxyl groups; and acid anhydrides of carboxylic acids.

The cellulose acetate butyrate is prepared by substituting certain of the butyryl groups for acetyl groups in the cellulose acetate.

The invention described herein makes possible the objects of (1) providing a novel and useful moisture sensitive material, the impedance of the moisture sensor of which is substantially represented by a first-order function of the relative humidity ranging from 0% to 100%, that is, a linear relationship exists between the impedance and the relative humidity, resulting in an inexpensive moisture sensor having a simplified signal processing network; (2) providing a moisture sensitive material used in a moisture sensor which exhibits an excellent stable moisture sensitive characteristic and an excellent water resistance even in a high humidity atmosphere; (3) providing a moisture sensitive material having an excellent resistance to organic chemicals such as animal oils, plant oils, mineral oils, aliphatic hydrocarbons, aromatic hydrocarbons, alcohols, ethers, esters, ketones, etc., (4) providing a moisture sensitive material for a fine patterned moisture sensor which can be produced by photolithography, etc. without deterioration of the moisture sensitive characteristic; (5) providing a moisture sensitive material for a moisture sensor having a small hysteresis of the moisture sensitive characteristic curve; (6) providing a moisture sensitive material for a moisture sensor which is excellent in response; (7) providing a moisture sensitive material, by which a moisture sensitive film is easily formed for each wafer unit; and (8) providing a moisture sensitive material for a moisture sensor which is uniform in quality because the number of moisture sensors to be formed for a wafer can be increased due to the minimization of the size of the moisture sensitive film.

BRIEF DESCRIPTION OF THE DRAWINGS

This invention may be better understood and its numerous objects and advantages will become apparent to those skilled in the art by reference to the accompanying drawings as follows.

DESCRIPTION OF THE PREFERRED EMBODIMENTS

Figure 1:
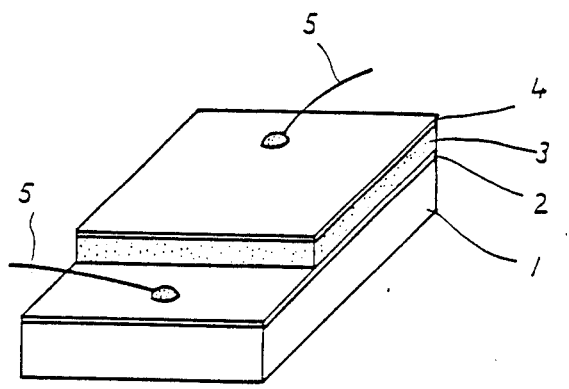
FIG. 1 is a scheme illustrating a moisture sensor manufactured for evaluation of the relationship between the impedance and the relative humidity characteristic with respect to a moisture sensitive material of this invention.

FIG. 1 shows a scheme of a moisture sensor used for evaluation of the electric characteristic of a moisture sensitive material according to this invention. The moisture sensor is manufactured by the following processes: On a substrate 1 made of an insulator such as glass, alumina or the like, or a semiconductor such as silicon or the like, a single-layered metal conductive film such as gold, platinum or the like, or a double-layered metal conductive film such as gold and titanium or chromium or the like is formed by a vacuum evaporation technique or by a spattering method to form a bottom electrode 2. As the substrate 1, a metal board may be used, which serves as a bottom electrode. Then, a moisture sensitive film 3 is formed on the bottom electrode 2. On the moisture sensitive film 3, a moisture permeable conductive film made of gold, chromium or the like is formed by a vacuum evaporation technique or by a spattering method to form an upper electrode 4. A lead wire 5 is connected to the bottom electrode 2 and another lead wire 5 is connected to the upper electrode 4 thereby constituting a pair of detecting electrodes, through which an electric current flows to determine variation of the impedance of the moisture sensitive film 3.

Although a conventional moisture sensor having a moisture sensitive film made of a hydrophilic polymer or a polyelectrolyte can be easily provided at low cost due to its simple structure and easy production, it is inferior in stability of the moisture sensitive characteristic over a long period of time and durability because the film has insufficient moisture and/or water resistances due to its hydrophilic nature. On the other hand, a crosslinked cellulose acetate butyrate film is inherently insoluble in water and is not easily disolved, maintaining its quality, even under severe conditions such as prolonged exposure to a high humidity atmosphere or water; that is, a moisture sensitive film made of a crosslinked cellulose acetate butyrate film maintains a stable moisture sensitive characteristic even in a high humidity atmosphere having a relative humidity of from 90% to 95% or more or in the case where dew condensation arises on the surface of the film. Thus, the use of the crosslinked cellulose acetate butyrate film for the moisture sensitive film 3 shown in FIG. 1 overcomes such drawbacks of the conventional moisture sensitive film made of a hydrophilic polymer or a polyelectrolyte in which the moisture sensitive characteristic of the film deteriorates due to a high humidity in the atmosphere or dew condensation.

The resulting moisture sensor, in which a crosslinked cellulose acetate butyrate film is used for the moisture sensitive film 3, detects a variation of the dielectric constant of the film, by a pair of detecting electrodes, based on water-molecule absorption to or water-molecule desorption from the film.

With an increase in the acetification (the percentage of the conversion of the OH group into OCOCH$_3$ group) of cellulose acetate, the number of OH groups (hydrophilic groups) therein is reduced and the water-molecule absorption rate thereof is reduced so that the water-molecule absorption thereto or the water-molecule desorption therefrom takes place smoothly. Moreover, the process is reversible so that the difference (i.e., hysteresis) of the moisture sensitive characteristic between the hygroscopic step and the dehumidification step is small. However, due to the reduced number of OH groups, a necessary amount of crosslinking agents reacts insufficiently with OH groups in cellulose acetate, resulting in a crosslinked cellulose acetate which is inferior in resistance to organic solvents. On the contrary, cellulose acetate butyrate, which is prepared by substituting certain of the butyryl groups represented by the formula

for acetyl groups represented by the formula

in cellulose acetate, has a low rate of water-molecule absorption even though its OH group content is equal to that of cellulose acetate, so that hysteresis is small and a crosslinking reaction by crosslinking agents can proceed sufficiently.

Due to the fact that the hygroscopic nature of the crosslinked cellulose acetate butyrate film is relatively small and the impedance variation of the moisture sensor depends upon a variation of the dielectric constant of the moisture sensitive film which is based on water-molecule absorption to or water-molecule desorption from the film, a moisture sensor using a crosslinked cellulose acetate butyrate film as a moisture sensitive film has a characteristic that the impedance thereof is substantially represented by a first-order function of the relative humidity ranging from 0% to 100%, especially a linear relationship exists in a relative humidity of 20% or more. Thus, the moisture sensor does not need a logarithmic conversion processing network, so that the size can be minimized and it can be manufactured at a low cost.

Intelligent sensors such as microchip sensor devices or the incorporation of sensors with signal processing networks will require minimized patterned moisture sensors. To meet such a requirement by a photolithographic technique, the moisture sensor must be subjected to a patterning process, which will require it to be immersed in organic chemicals such as acetone. Accordingly the moisture sensor must have a sufficient resistance to organic chemicals.

While cellulose acetate butyrate is nonsoluble in water, animal oils, plant oils, mineral oils, aliphatic hydrocarbons, aromatic hydrocarbons, esters, etc., it is soluble in some organic chemicals such as methyl acetate, acetone, ethylene glycol monomethyl ether acetate, etc. Thus, it is most important that polymer chains in the cellulose acetate butyrate film can be three-dimensionally bonded with each other to restrict the freedom of the chains without damaging the moisture sensitive characteristic of the cellulose acetate butyrate film thereby preventing the cellulose acetate butyrate from eluting to the outside, resulting in a moisture sensitive film having an improved resistance to organic chemicals. However, when the chemical bonding among the polymer chains is too strong, the moisture sensitive film will crack due to a hygroscopic swelling. To avoid this phenomenon, chemical bonding should take place in order to insure sufficient resilience, which can be attained by a crosslinking technique by which polymer chains are crosslinked with other chain molecules (crosslinking molecules). A moisture sensitive material according to this invention, which has an excellent resistance to organic chemicals, is prepared by crosslinking cellulose acetate butyrate with at least one compound selected from the group consisting of compounds containing two or more isocyanate groups represented by the formula —N=C=O; compounds containing two or more epoxy groups represented by the formula

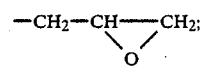

compounds containing two or more carboxyl groups represented by the formula

and acid anhydrides of carboxylic acids. Examples of isocyanate compounds are polyisocyanate (Trade name: COLONATE L, manufactured by Nippon Polyulethane Kogyo K.K., Japan) and tolylenediisocyanate. Examples of epoxy compounds are 1.3-butadienediepoxide manufactured by Tokyo Kasei Kogyo K.K., Japan) and 1.7-octadienediepoxide (manufactured by Tokyo Kasei Kogyo K.K., Japan). As carboxyl compounds, terephthalic acid can be used. As acid anhydrides of carboxylic acids, phthalic anhydride and maleic anhydride can be used.

EXAMPLE 1

Cellulose acetate butyrate is admixed with an isocyanate compound (e.g., polyisocyanate manufactured by Nippon Polyulethane Kogyo K.K., Japan) as a crosslinking agent in a ratio of 10 to 1 by weight. The mixture is dissolved in ethylene glycol monomethyl ether acetate with an adequate viscosity, and the resulting solution is coated, by a spinner printing method or an immersion method, on the bottom electrode 2 of gold or the like, which is formed on the glass electrode 1 by a vacuum evaporation technique, to form a thin film or a thick film thereon, which is then air-dried and followed by a heat treatment at a temperature of 100° C. to 200° C. to form the moisture sensitive film 3 made of a crosslinked cellulose acetate butyrate film. The temperature in the heat treatment process in the formation of the moisture sensitive film 3 using cellulose acetate butyrate depends upon the solvent used therefor. When the temperature is excessively low, the film obtained is not tough or the crosslinking reaction by the crosslinking agent does not proceed sufficiently, resulting in a moisture sensitive film which is inferior in resistance to organic chemicals. On the contrary, cellulose acetate butyrate generally starts to decompose upon heating at 230° C. or higher and changes its moisture sensitive characteristic. Thus, in order to obtain a moisture sensitive film having an excellent moisture sensitive characteristic, the heat-treatment should be carried out at a temperature ranging from around 100° C. to around 200° C.

In this example, the heat-treatment was carried out at 150° C. for 2 hours in a nitrogen atmosphere to form a moisture sensitive film having a thickness of about 1 $\mu$m. On the moisture sensitive film 3, a moisture permeable thin gold film having a thickness of approximately 200 Å was formed as the upper electrode 4. The upper electrode 4 and the bottom electrode 2, respectively, were connected to a detecting circuit by lead wires 5, resulting in a moisture sensor.

Figure 2:
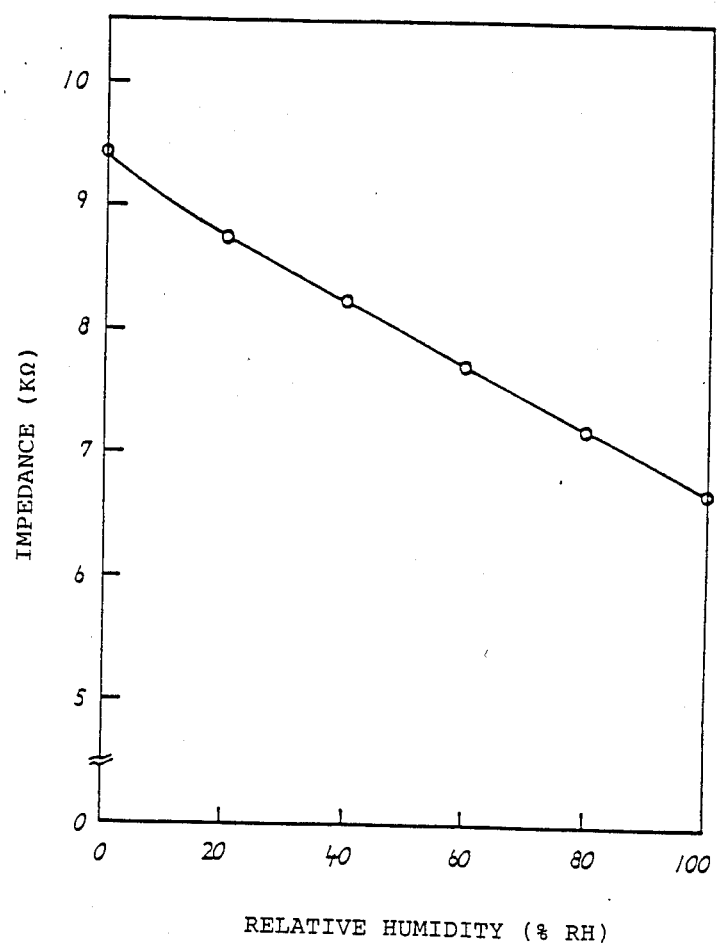
FIG. 2 is a graph of the moisture sensitive characteristic of the moisture sensor shown in FIG. 1.

FIG. 2 shows a moisture sensitive characteristic curve (illustrating the relationship between the impedance and the relative humidity) at a time when alternating current having a voltage of 0.1 V and a frequency of 10 KHz is applied to the moisture sensor at a temperature of 25° C. It indicates that a linear relationship exists between the impedance and the relative humidity ranging from 0% to 100% of the relative humidity, especially, in the region of 20% or more of relative humidity. Even when the moisture sensor is allowed to stand in a high temperature (60° C.) and high humidity (90-95%RH) atmosphere for over 1,000 hours, variation of the impedance in each of the relative humidities is hardly observed. This indicates that the moisture sensitive material according to this invention is stable even in a high temperature and high humidity atmosphere.

The crosslinked cellulose acetate butyrate film was also subjected to an organic chemical-resistance test to examine the effect of an acetone-immersion treatment on the moisture sensitive material on the characteristics of the moisture sensor. As a moisture sensitive material, a crosslinked cellulose acetate butyrate film and an uncrosslinked cellulose acetate butyrate film were prepared for the test, each of which was immersed in acetone. On each of the acetone treated films, an upper electrode was formed to produce two kinds of moisture sensors. Two more kinds of moisture sensors were produced, one using a crosslinked cellulose acetate butyrate film and the other using an uncrosslinked cellulose acetate butyrate film, neither of which were treated with acetone. Influences of the acetone-treatment on the moisture sensitive characteristic of each of these moisture sensors were examined. The moisture sensitive characteristic of the moisture sensor having the crosslinked cellulose acetate butyrate film treated with acetone is hardly different from that of the moisture sensor having the crosslinked cellulose acetate butyrate film untreated with acetone, while the moisture sensitive characteristic of the moisture sensor having the uncrosslinked cellulose acetate butyrate film treated with acetone cannot be evaluated because the components of the uncrosslinked cellulose acetate butyrate were eluted in the acetone.

As mentioned above, the crosslinked cellulose acetate butyrate film prepared in this example has a stable moisture sensitive characteristic and a sufficient organic chemical resistance, which are proved by the fact that the film is not damaged under severe conditions such as an acetone-immersion treatment.

EXAMPLE 2

Cellulose acetate butyrate was admixed with dicarboxylic acid (e.g., terephthalic acid) in a ratio of 5 to 2 by weight. The mixture was dissolved in a dimethyl sulfoxide solution with an adequate viscosity. Using the resulting solution, a moisture sensitive film was formed, in the same manner as in Example 1, to produce a moisture sensor. The moisture sensitive characteristic of the moisture sensor was examined, in the same manner as in Example 1, indicating that a linear relationship exists between the impedance and the relative humidity in the whole range of 0% to 100% of the relative humidity. The moisture sensor was also subjected to the same tests as in Example 1, for one of which the moisture sensor was allowed to stand in a high temperature and high humidity atmosphere, and for the other of which the moisture sensor was treated with organic chemicals, confirming that the moisture sensitive characteristic of the sensor did not vary.

EXAMPLE 3

Cellulose acetate butyrate was admixed with an epoxy compound (e.g., 1.3-butadienediepoxide or 1.7-octadienediepoxide, both of which are manufactured by Tokyo Kasei Kogyo K.K., Japan) as a crosslinking agent in the ratio of 5 to 2 by weight. The mixture was then dissolved in a dimethyl sulfoxide solution with an adequate viscosity. Using the resulting solution, a moisture sensitive film was formed, in the same manner as in Examples 1 and 2, to obtain a moisture sensor, which was then subjected to the same tests as in Examples 1 and 2 which gave the same excellent results as in Examples 1 and 2.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty which reside in the present invention, including all features which would be treated as equivalents thereof by those skilled in the art to which this invention pertains.

What is claimed is:

1. A moisture sensitive material prepared by cross-linking cellulose acetate butyrate with at least one compound selected from the group consisting of compounds containing two or more isocyanate groups; compounds containing two or more epoxy groups; compounds containing two or more carboxyl groups; and acid anhydrides of carboxylic acids; said cross-linking being sufficient so that the sensitivity of said moisture sensitive material is not damaged upon acetone immersion, the weight ratio of said cellulose acetate butyrate to said selected compound or compounds being in the range of 10:1 to 5:2, said moisture sensitive material characterized by a linear relationship between the impedance of said moisture sensor and the relative humidity in the range of 20% to 100% of the relative humidity.

2. The moisture sensor according to claim 1, wherein said cellulose acetate butyrate is prepared by substituting certain of the butyryl groups for acetyl groups in the cellulose acetate.

3. The moisture sensor according to claim 1, wherein said moisture sensitive material is prepared by cross-linking cellulose acetate butyrate with at least one compound containing two or more isocyanate groups.

4. The moisture sensor according to claim 1, wherein said moisture sensitive material is prepared by cross-linking cellulose acetate butyrate with a compound containing two or more epoxy groups.

5. The moisture sensor according to claim 1, wherein said moisture sensitive material is prepared by cross-linking cellulose acetate butyrate with a compound containing two or more carboxyl groups.

6. The moisture sensor according to claim 1, wherein said moisture sensitive material is prepared by cross-linking cellulose acetate butyrate with an acid anhydride of a carboxylic acid.

7. A moisture sensor comprising a substrate, a bottom electrode disposed of said substrate, a moisture sensitive film disposed of said bottom electrode, an upper electrode disposed of said moisture sensitive film, and lead wires connected to said bottom electrode and said upper electrode, respectively, to form a pair of detecting electrodes through which electric current flows to determine a variation of the impedance of said moisture sensitive film, said film being made of a moisture sensitive material prepared by cross-linking cellulose acetate butyrate with at least one compound selected from the group consisting of compounds containing two or more isocyanate groups; compounds containing two or more epoxy groups; compounds containing two or more carboxyl groups; and acid anhydrides of carboxylic acids, said cross-linking being sufficient so that the sensitivity of said moisture sensitive material is not damaged upon acetone immersion, the weight ratio of said cellulose acetate butyrate to the selected compound or compounds being in the range from 10:1 to 5:2, said moisture sensitive material characterized by a linear relationship between the impedance of said moisture sensor and the relative humidity in the range of 20% to 100% of the relative humidity.

8. A moisture sensor according to claim 7, wherein the dielectric constant of said moisture sensitive material varies with the absorption and the desorption of water vapor or moisture, so that the electrostatic capacity between said electrodes varies therewith, to thereby detect a variation of humidity in the atmosphere.

9. A moisture sensor comprising a substrate, a bottom electrode disposed of said substrate, a moisture sensitive film disposed of said bottom electrode, an upper electrode disposed of said moisture sensitive film, and lead wires connected to said bottom electrode and said upper electrode, respectively, to form a pair of detecting electrodes to detect a variation of electrostatic capacity between said electrodes, the dielectric constant of said moisture sensitive film varying with the absorption and desorption of water vapor or moisture, said film being made of a moisture sensitive material prepared by cross-linking cellulose acetate butyrate with at least one compound selected from the group consisting of compounds containing two or more isocyanate groups; compounds containing two or more epoxy groups; compounds containing two or more carboxyl groups; and acid anhydrides of carboxylic acids, said cross-linking being sufficient so that the sensitivity of said moisture sensitive material is not damaged upon acetone immersion, the weight ratio of said cellulose acetate butyrate to the selected compound or compounds being in the range from 10:1 to 5:2, said moisture sensitive material characterized by a linear relationship between the impedance of said moisture sensor and the relative humidity in the range of 20% to 100% of the relative humidity.

10. The moisture sensor according to claim 9, wherein said moisture sensitive film is prepared by cross-linking cellulose acetate butyrate with at least one compound containing two or more isocyanate groups.

11. The moisture sensor according to claim 9, wherein said moisture sensitive film is prepared by cross-linking cellulose acetate butyrate with a compound containing two or more epoxy groups.

12. The moisture sensor according to claim 9, wherein said moisture sensitive film is prepared by cross-linking cellulose acetate butyrate with a compound containing two or more carboxyl groups.

13. The moisture sensor according to claim 9, wherein said moisture sensitive film is prepared by cross-linking cellulose acetate butyrate with an acid anhydride of a carboxylic acid.

14. In a moisture sensor containing a moisture sensitive material, the improvement wherein said moisture sensitive material is prepared by cross-linking cellulose acetate butyrate with at least one compound selected from the group consisting of compounds containing two or more isocyanate groups; compounds containing two or more epoxy groups; compounds containing two or more carboxyl groups; and acid anhydrides of carboxylic acids; said cross-linking being sufficient so that the sensitivity of said moisture sensitive material is not damaged upon acetone immersion, the weight ratio of said cellulose acetate butyrate to said selected compound or compounds being in the range of 10:1 to 5:2, said moisture sensitive material characterized by a linear relationship between the impedance of said moisture sensor and the relative humidity in the range of 20% to 100% of the relative humidity.

15. The moisture sensor according to claim 14, wherein said cellulose acetate butyrate is prepared by substituting certain of the butyryl groups for acetyl groups in the cellulose acetate.

16. The moisture sensor according to claim 14, wherein said moisture sensitive material is prepared by cross-linking cellulose acetate butyrate with at least one compound containing two or more isocyanate groups.

17. The moisture sensor according to claim 14, wherein said moisture sensitive material is prepared by cross-linking cellulose acetate butyrate with at least one compound containing two or more epoxy groups.

18. The moisture sensor according to claim 14, wherein said moisture sensitive material is prepared by cross-linking cellulose acetate butyrate with at least one compound containing two or more carboxyl groups.

19. The moisture sensor according to claim 14, wherein said moisture sensitive material is prepared by cross-linking cellulose acetate butyrate with at least one acid anhydride of a carboxylic acid.

* * * * *